(12) United States Patent
Wakalopulos

(10) Patent No.: US 9,744,320 B2
(45) Date of Patent: Aug. 29, 2017

(54) ELECTRIC WICK AND HEATER FOR PORTABLE VAPORIZER

(71) Applicant: George Wakalopulos, Pacific Palisades, CA (US)

(72) Inventor: George Wakalopulos, Pacific Palisades, CA (US)

(*) Notice: Subject to any disclaimer, the term of this patent is extended or adjusted under 35 U.S.C. 154(b) by 425 days.

(21) Appl. No.: 14/534,468

(22) Filed: Nov. 6, 2014

(65) Prior Publication Data

US 2015/0217068 A1 Aug. 6, 2015

Related U.S. Application Data

(60) Provisional application No. 61/935,644, filed on Feb. 4, 2014.

(51) Int. Cl.
*A61M 15/06* (2006.01)
*H05B 1/02* (2006.01)
*A24F 47/00* (2006.01)
*A61M 11/04* (2006.01)

(52) U.S. Cl.
CPC ......... *A61M 15/06* (2013.01); *A24F 47/008* (2013.01); *A61M 11/044* (2014.02); *H05B 1/0244* (2013.01); *A61M 2205/3653* (2013.01); *A61M 2205/8206* (2013.01)

(58) Field of Classification Search
CPC ........... A61M 11/044; A61M 15/06; A61M 2205/8206; A24F 47/002; A24F 47/004; A24F 47/008
See application file for complete search history.

(56) References Cited

U.S. PATENT DOCUMENTS

| | | | | |
|---|---|---|---|---|
| 5,819,756 | A * | 10/1998 | Mielordt | A24F 47/008 131/194 |
| 2013/0213419 | A1 | 8/2013 | Tucker et al. | |
| 2014/0190496 | A1* | 7/2014 | Wensley | A24F 47/008 131/273 |
| 2014/0261486 | A1* | 9/2014 | Potter | A24F 47/008 131/328 |
| 2014/0373857 | A1* | 12/2014 | Steinberg | A24F 47/008 131/329 |
| 2015/0196060 | A1* | 7/2015 | Wensley | F22B 1/288 392/390 |

\* cited by examiner

*Primary Examiner* — Lynne Anderson
(74) *Attorney, Agent, or Firm* — Thomas Schneck

(57) ABSTRACT

A resistive foil heater for a portable inhaler. A reservoir of vapor material, usually a fluid, has transport by the foil to directly heat the material to a temperature sufficient to vaporize the material to the gas phase. The foil may have a dimpled plate shape, or box shape, a capillary or parallel plate shape.

2 Claims, 6 Drawing Sheets

ELECTRIC WICK AND HEATER FOR PORTABLE VAPORIZER

CROSS-REFERENCE TO RELATED APPLICATION

This application claims priority from U.S. provisional application Ser. No. 61/935,644, filed Feb. 4, 2014.

TECHNICAL FIELD

The invention relates to an electrical vaporizer for an electronic cigarette or medicinal inhaler.

BACKGROUND ART

The wick has been used for thousands of years to provide lighting in darkness and has progressed in the past several centuries in kerosene lamps and candles. The operation of a wick, in its basic form, utilizes capillary action, in which a liquid is transported inside a small diameter passage, by attractive forces between the passage material and the liquid properties. For example, if a small diameter glass tube is inserted into a water container, the water will rise inside the tube, to a height which is proportional to the difference in surface tension, of the glass and water, and inversely proportional to the tube diameter and the liquids' viscosity. Capillary action is one of the fundamental processes in transporting water in trees from the ground to the leaves.

In a wick, the cohesive forces between the wick fibers and the liquid surface tension, transport the liquid material upwards, thus increasing the liquid materials' surface area and causing it to evaporate by a heat source such as a candle flame or electric powered wire filament. In a wire filament, such as that described in the U.S. Publication No. 2013/0213419A1, entitled "Electronic Smoking Article and Improved Heater Element", by C. S. Tucker et al., a wire mesh, instead of a wire, is utilized as the heat source, vaporizing the liquid transported by the wick, from the liquid reservoir. The wire mesh, having a greater surface area, is thus more efficient in vaporizing the liquid in contact with the wick material, than a circular wire.

The concern with such vaporization methods, is that the heat source is in contact with the wick material, and one the liquid is depleted, the heater elements' temperature rises sufficiently to combust the wick material causing potentially toxic vapors to be generated. FDA and WHO regulators are concerned, but may be years away from issuing any regulations regarding e-cigarettes and vaporizers.

SUMMARY OF INVENTION

The present invention utilizes thin resistive foils instead of wires or wire meshes, to vaporize the wax, liquid, or solid materials to be vaporized in an inhaler. Due to the larger surface area of the foils, they can vaporize equal amounts of material, per unit power, with a lower temperature, and thus minimizing the combustion of the wick, when the liquid material is depleted.

Many devices employed for aromatic therapy or vaporization utilize resistive wire heating elements or massive plates heated by conduction from resistive wire heaters. These heating methods dissipate more energy to reach the desired temperature for vaporization due the requirement of elevating the temperature of the container which contains the material to be vaporized.

In contrast, if the heating element is also the container or wick of the vaporizable material, and also if the heating element has ultra low mass, the energy required to reach the desired temperature is minimized and thus portable vaporization devices can be made which are powered by batteries. Another advantage of ultra low mass heaters is virtually instant on off heating capability which allows for precise temperature control which is essential to extract only the low temperature vapor, and not burn the material, which causes harmful or carcinogenic gases to be generated.

In another embodiment of the invention, by spiraling or folding the resistive foil material, capillary passages formed by the thin foil are maintained in communication with a vaporizable liquid. The liquid media is transported to the heating element surface, where it is vaporized, by capillary action without a wick, thus eliminating the combustion of the organic wick material. In this design, however, the surface of the foil material must be oxidized, to form an insulating barrier, to keep the contacting metal layer from shorting out between each other.

In yet another embodiment of the invention, thin ceramic sheets (10-12 micrometers) are processed for high surface tension for capillary action, the heated with thick films, to achieve vaporization of the liquid material.

DETAILED DESCRIPTION

Figure 1:
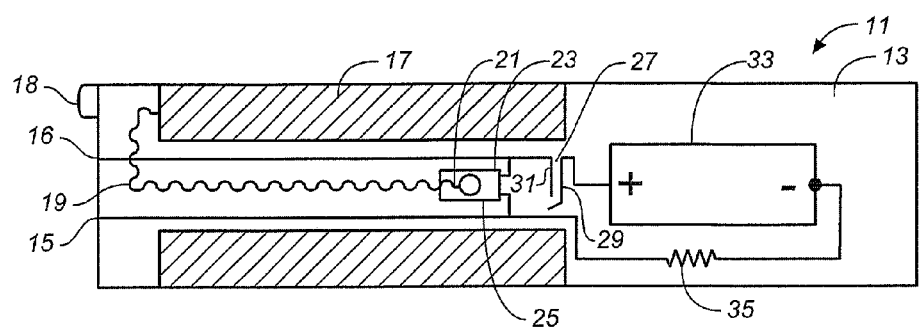
FIG. 1 is a plan view of an e-cigarette or inhaler having a foil heater of the present invention.

With reference to FIG. 1, a vaporizer 11 is shown having a housing 13 that has a common cigarette form factor, and would be useful as a medicinal inhaler or an electronic cigarette. The housing 13 is cylindrical with a central axis of symmetry. The housing may be plastic or glass. Within the housing, a coaxial inhalation tube 15 extends proximately 60 percent of the length of the housing. The inhalation tube has an end 16 in common with the end 18 of housing 13 intended to be near the lips of the user.

Within the housing 13, but spaced from housing end 18 is a fluid reservoir 17 which is coaxial with housing 13. Reservoir 17 may be semi-rigid sponge material that holds a supply of inhalation material, usually a fluid, such as propylene glycol, that can flow within the reservoir material in response to pressure drops. A pressure drop is established by a capillary tube 19 that extends into the reservoir material near housing end 18 and extends from the reservoir along the access of the housing to a heater foil panel 21 which is a thin film of conductive material, such as aluminum. The diameter of capillary tube is several microns in a hollow glass fiber. The distant end of the fiber is adhered to the foil 21.

Foil 21 is thin film panel that is less than 50 microns thick. The panel can be planar, but preferably has a dimple or well for holding a supply of inhalation material fluid received from the capillary tube 19. The panel is approximately two square millimeters in area and is supported on opposite sides by wires 23 and 25, with the dimple or well being centrally located between the wires. The conductive wires 23 and 25 extend rearwardly from opposites sides of the conductive panel towards battery 33. Conductive wire 23 terminates at a pressure switch 27 having a first switch member 29 which is a hinged leaf spring that is spaced a small distance from the second switch member 31 which is an arm connected to the conductive wire 23. When a user inhales through the inhalation tube 15, the pressure switch closes because the hinged leaf spring member 29 contacts the second switch member 31 thereby closing the switch. This causes wire 23 to be an electrical communication with the positive terminal of battery 33. The negative side of battery 33 is connected through a resistor 35 to wire 25 on the opposite side of foil panel 21 from the wire 23. Closing of the switch 27 causes current to flow through resistor 35 and across the foil 21, causing resistive heating of the foil while the switch is closed. Because the foil is very thin, its resistance is relatively high causing the heater to sufficiently hot to vaporize the inhalation material fluid that is supported on the foil, particularly in a foil well if provided. Resistance of the foil is between 0.2 and 0.5 ums. Temperature of the foil can reach 1,200 degrees F. if no liquid is on the foil. With liquid on the foil, the temperature of the foil ranges between 400 and 600 degrees F. which is sufficiently for vaporization of the liquid. The higher temperatures that arise without liquid are adequate for cleaning the foil in instances where there could be a momentary gap in delivery of fluid from the capillary tube 19. Since the reservoir is removed from the foil, there is no combustion and no inhalation of foreign materials. The inhaler of the invention operates until the reservoir is depleted.

Figure 2:
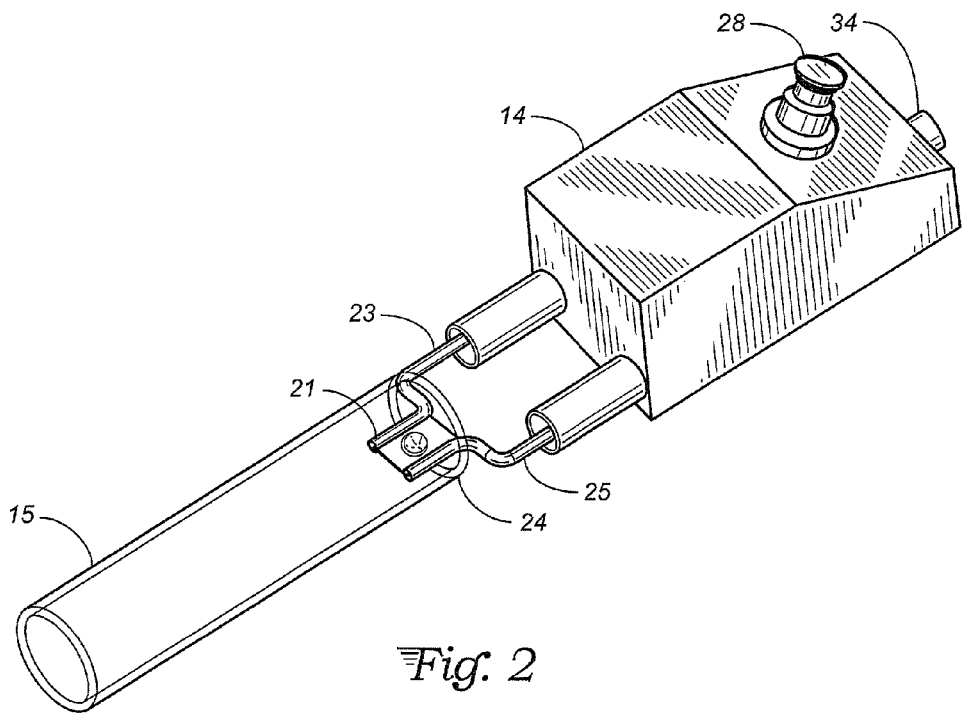
FIG. 2 is an electric plan of the foil heater of FIG. 1.

In FIG. 2, an alternate embodiment is shown. As before the foil panel 21 is mounted near an end of the glass inhalation tube 15. The fluid reservoir, capillary end housing are not shown. The foil is supported within the inhalation tube by an insulative ring 24 mounted to the end of the inhalation tube 15. Wires 23 and 25 provide power to opposites sides of the thin film foil panel 21. Power is supplied to the foil by an adjustable, constant voltage power supply 14 that has a manual on-off switch 28, operated by a push button that extends through the housing. When the housing is gripped by the fingers, a finger can push down on the switch creating momentary heating of the foil and vaporizing fluid which has been delivered to the foil panel 21. An external power supply is used to supply input DC voltage, typically 3 to 12 volts DC to connector 34. The connector has positive and negative terminals that supply the voltage to wires 23 and 25 responsive to actuation of switch 28.

Figure 3:
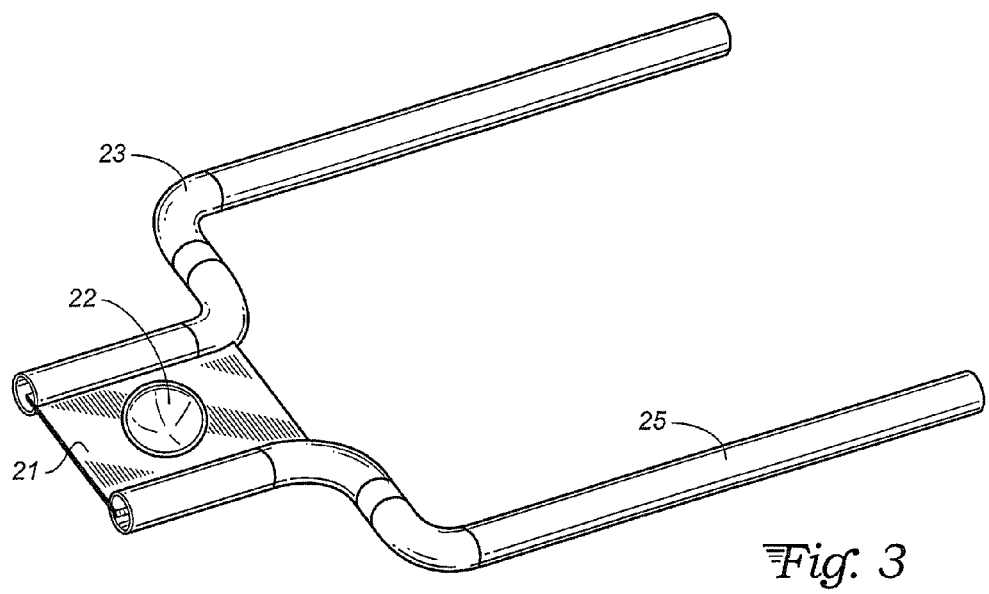
FIG. 3 is a perspective view of the foil heater of FIG. 2.

In FIG. 3, the foil panel is seen to be having a central dimple 22 that serves as a well for inhalation material, usually a fluid. A capillary delivers the fluid directly to the well. Opposite sides of the foil panel 21 are spot welded to the conductive wires 23 and 25.

Figure 4:
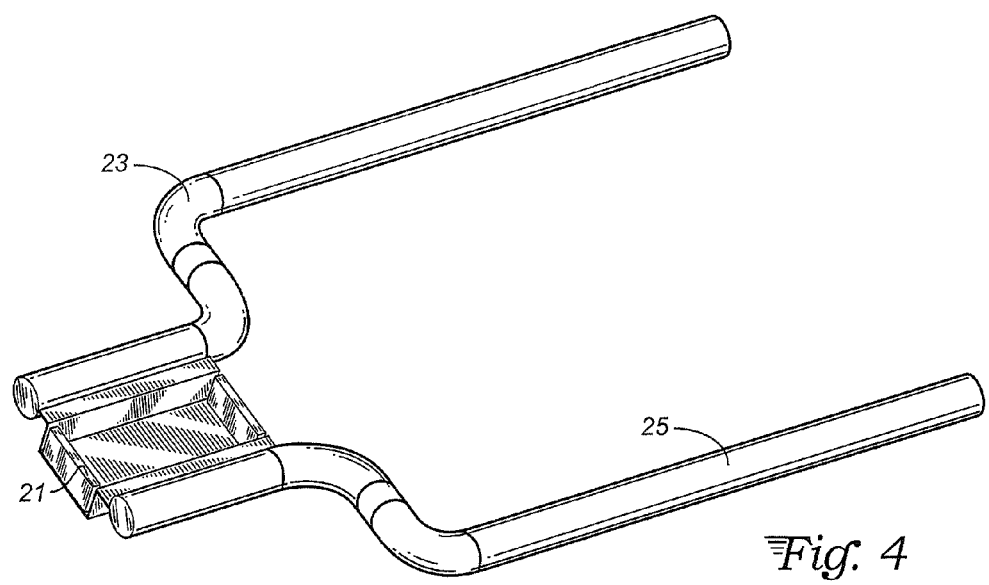
FIG. 4 is a perspective view of an alternate foil heater.

In FIG. 4, the wires 23 and 25 are seen to be connected to a box shaped foil panel 21 where the box serves as an inhalation material container. The box has four lateral sides and a bottom, but an open top. The open top receives inhalation material fluid from the capillary. Heating of the foil box panel to a temperature above 400 degrees F. causes vaporization of the fluid, thereby generating smoke. A preferred material for the foil is a nickel chromium alloy having temperature characteristics similar to Nichrome wire used in toasters.

Figure 5:
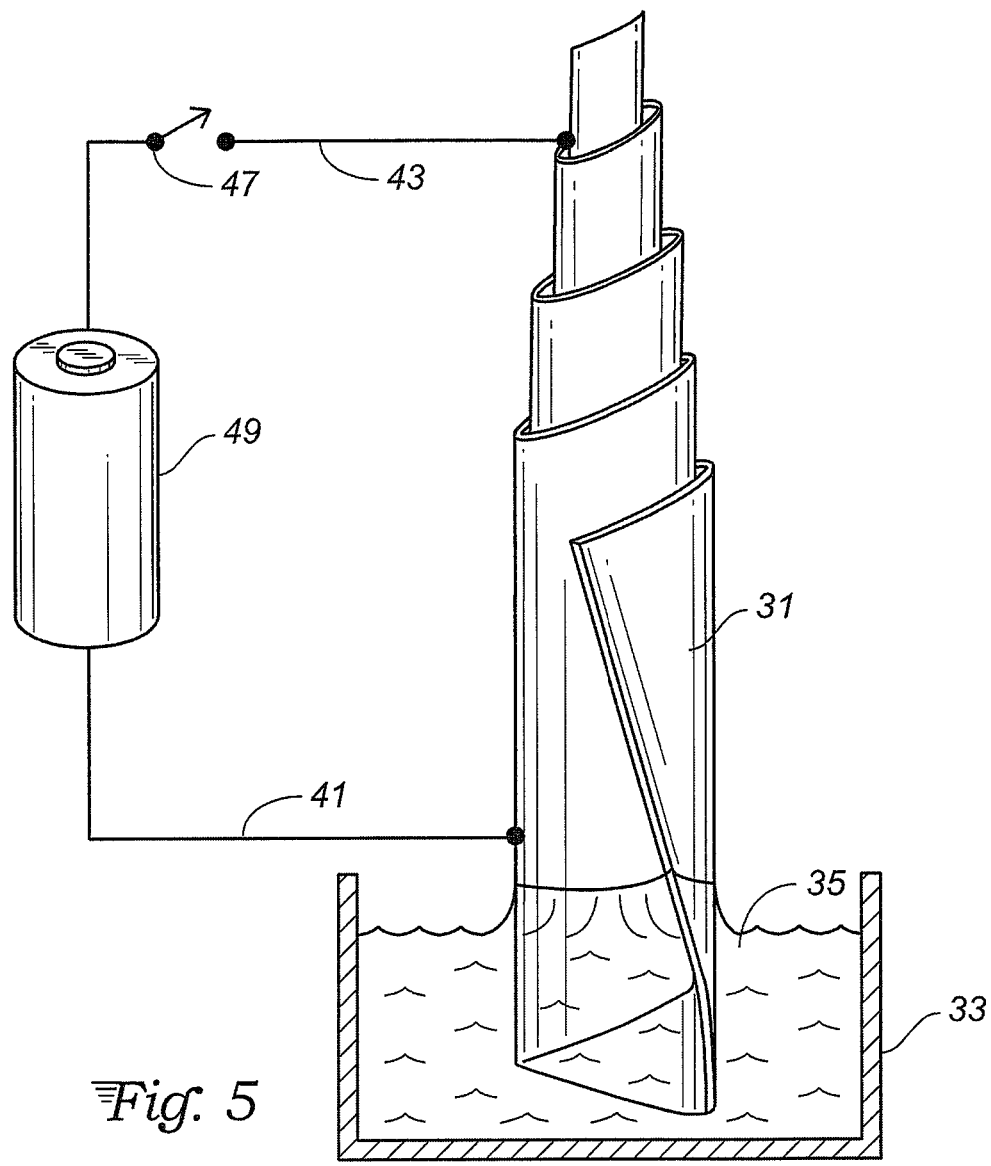
FIG. 5 is an electrical plan and heater side plan view of a capillary foil heater for a vaporizer.
Figure 5A:
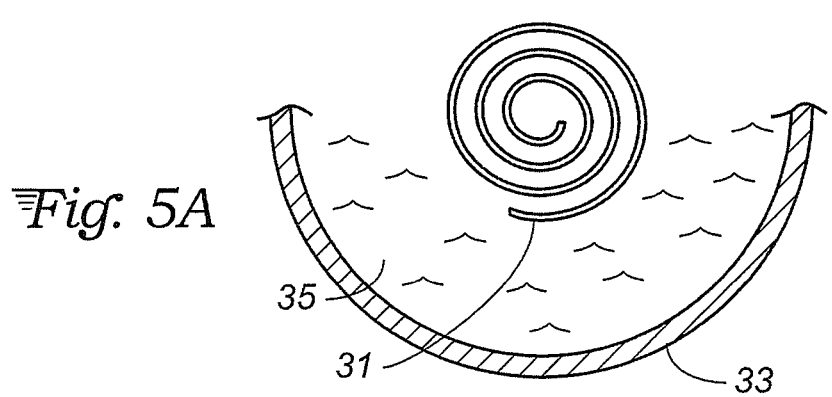
FIG. 5A is a top view of the apparatus of FIG. 5.

With reference to FIG. 5 a thin resistive foil 31 of the kind previously described has been wound in a spiral manner to form a capillary having a diameter appropriate for wicking liquid 35 from the liquid container 33. The foil has been oxidized so that conductive wires 41 and 43 will not short. Rather, the wires 41 and 43 make contact with the foil at reagents where the oxide has been removed in order to apply power from a battery 45 that actuated by a switch 47. As the spiral foil 31 wicks material upwardly, the foil is heated to 400 degrees C. or more and material within the capillary is vaporized by the heat and exits through the top of the capillary. In the top view of FIG. 5A the turns of the spiral foil are seen to be non-contacting due to oxide treatment of the foil that prevents shorting.

Figure 6:
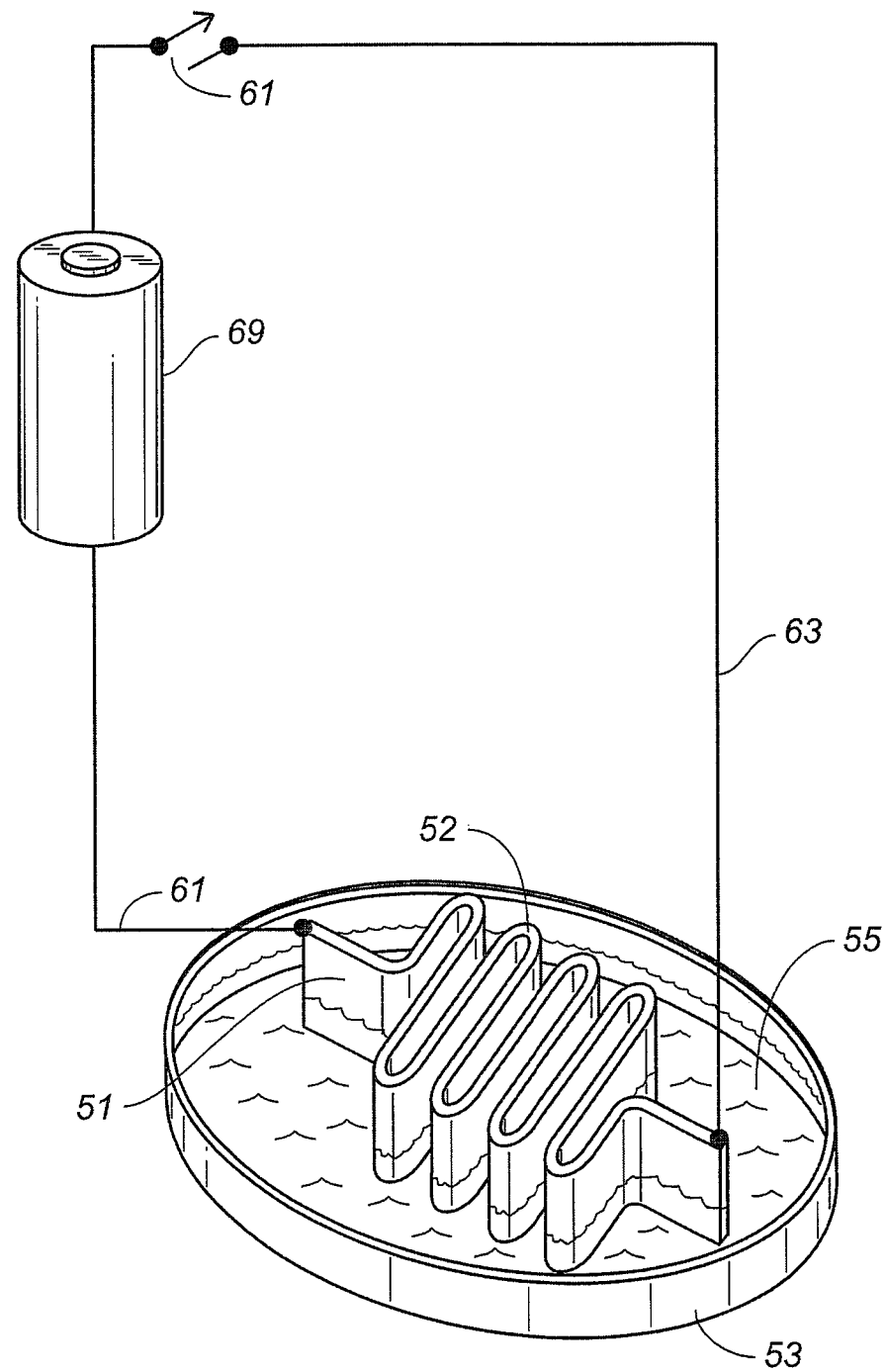
FIG. 6 is an electrical plan and heater perspective plan view of an alternate capillary foil heater for a vaporizer.

In FIG. 6, resistive foil 51 is seen to be accordion pleated and has oxide coatings on opposite sides of the foil. The pleats 52 are sufficiently closely spaced so that the wick liquid 55 from the liquid container 53. Wires 61 and 63 are connected to opposite ends of the pleats 52 at regions where oxide coatings are removed for good electrical contact with the resistive foil 51. The wires draw power from a battery 69 which can be momentarily actuated by a switch 67. Liquid 55 is drawn into the interstices between the pleats 52 where it is heated and vaporized, moving upwardly where it is drawn into an inhalation tube.

Figure 7:
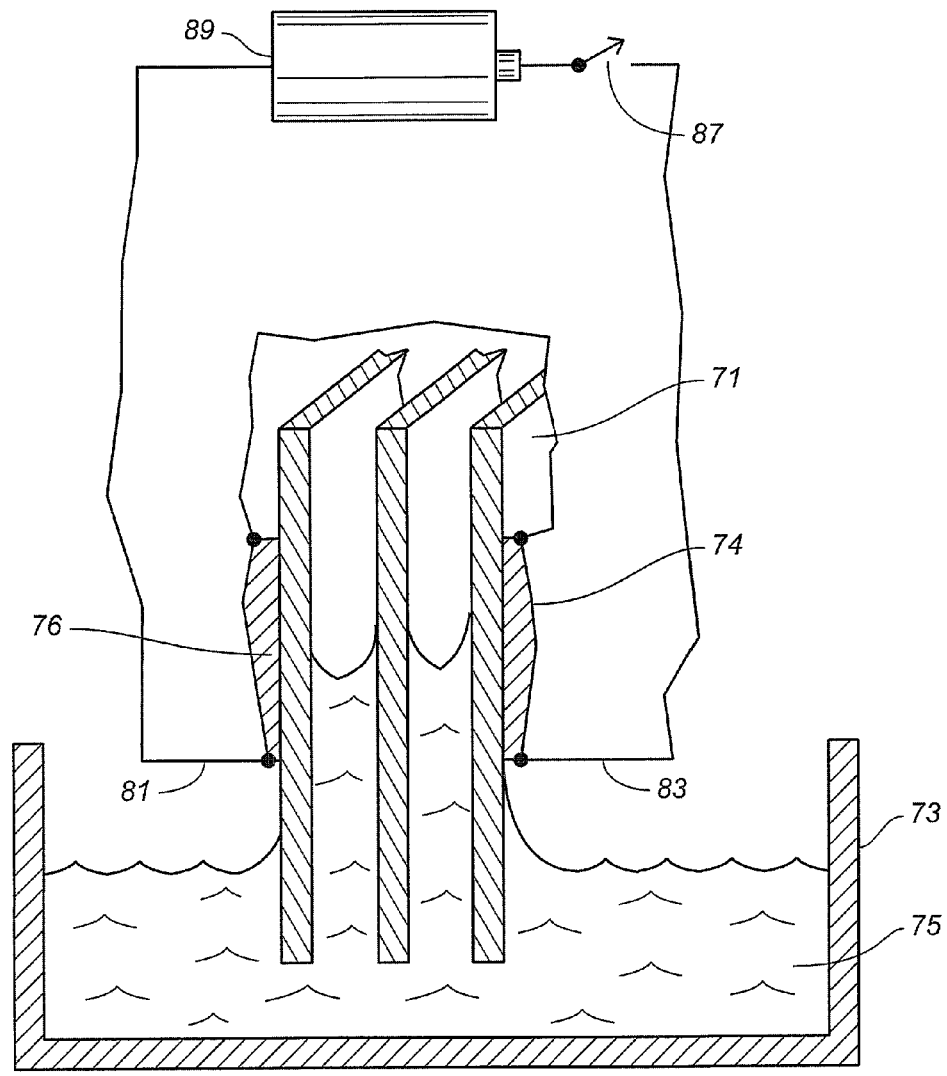
FIG. 7 is an electrical plan of another capillary heater for a vaporizer.

In FIG. 7, thin parallel ceramic plates 71 are spaced apart by a slight distance that allows capillary action with regard to liquid 75 that is in the liquid container 73. The thin ceramic plates have opposite sides to which thick film conductive members 74 and 76 are applied. For example, an aluminum film may be sputtered onto the ceramic plates for making electrical contact to wires 81 and 83 that are connected to opposite terminals of battery 89 that is actuated by switch 87. When the switch is actuated, current flows from the battery to the metal contacts 74 and 76, thereby heating the outward ceramic plates causing fluid between the plates that has been wicked upwardly to become vaporized. Vapor moves upwardly, causing further wicking of the liquid material so long as power is supplied by the battery. The ceramic plates are approximately the same size as the metal foil described with reference to FIG. 1, with a sufficient thickness to be self supporting.

Figure 8:
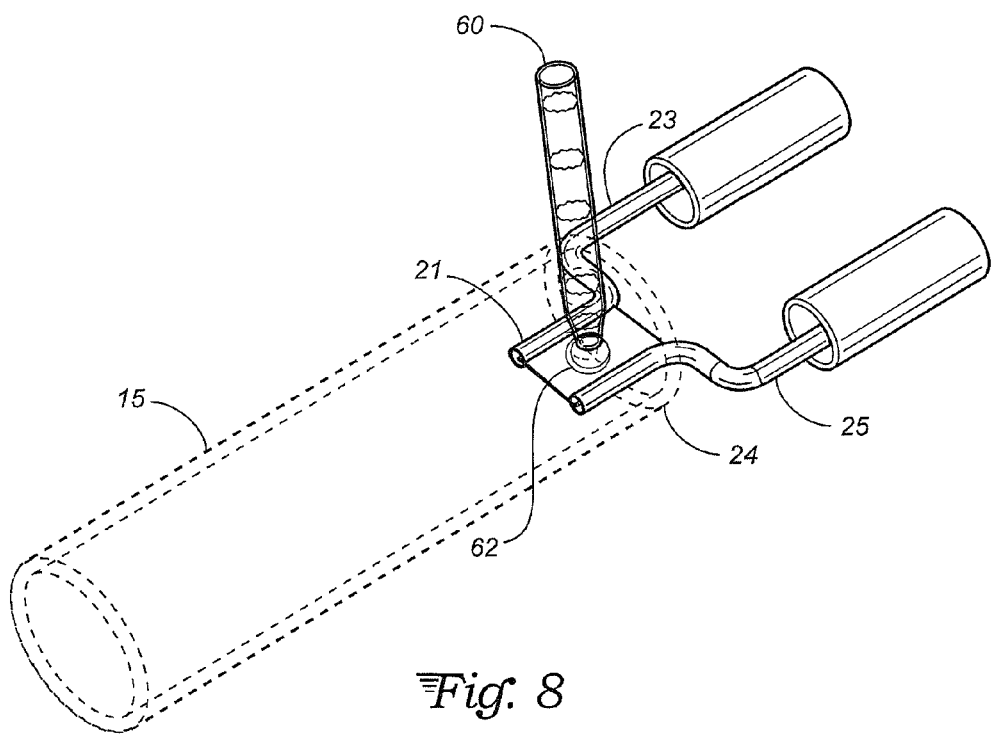
FIG. 8 is a perspective view of an alternate embodiment with gravity fed inhalation material fluid storage.

In the embodiment of FIG. 8, all elements are the same as in FIG. 2 except that a gravity fed inhalation fluid material storage tube 60 extends perpendicularly above inhalation tube 15. The fluid material flows by gravity onto a dimple 62 of the heated thin film foil panel 21. The storage tube 60 has a diameter of one to three millimeters and holds a few ml. of inhalation fluid material. The tube 60 is pushed in place into the circumferential periphery of inhalation tube 15 and may be removed when empty or no longer desired and replaced by a fresh inhalation fluid material storage tube of similar dimensions. The storage tube 60 is pushed down into inhalation tube 15 until the tip of the storage tube is a short distance from foil panel 21. As fluid material is vaporized from the heated foil panel, a drop of fluid material near the heated foil panel drops onto the panel for vaporization. Care must be taken so that vaporization does not occur in storage tube 60 and so the storage tube 60 must be a short distance from the heated foil panel. A tube indexing locator, not shown, may be placed above the heated foil panel to stop the downward motion of the storage tube 60 upon insertion into the inhalation tube 15 to prevent vaporization of inhalation fluid material in the storage tube.

What is claimed is:

1. A portable vaporizer for material to be inhaled drawn from a reservoir comprising:
- a heater having at least one planar panel formed of an electrically conductive foil mounted between two conductive legs extending toward a power supply, the foil having a thickness of less than 50 microns and an exposed area contacting material for vaporizing during electrical operation:
- a material fluid reservoir having an outlet in material delivery communication with the exposed area of the planar panel;
- the power supply and a switch connected to the two conductive legs, the switch connected to a power source with sufficient current output to the conductive legs heating the foil to a temperature vaporizing the material;
- a cigarette shaped housing having a user end and a distal end adapted for receiving airflow upon inhalation by a user and actuating the switch, the heater mounted closer to the user end than the power supply with an inhalation tube at the user end; and
- wherein the fluid reservoir coaxially surrounds at least a portion of the inhalation tube.

2. A portable vaporizer for material to be inhaled drawn from a reservoir comprising:
- a heater having at least one planar panel formed of an electrically conductive foil mounted between two conductive legs extending toward a power supply, the foil having a thickness of less than 50 microns and an exposed area contacting material for vaporizing during electrical operation;
- a material fluid reservoir having an outlet in material delivery communication with the exposed area of the planar panel;
- the power supply and a switch connected to the two conductive legs, the switch connected to a power source with sufficient current output to the conductive legs heating the foil to a temperature vaporizing the material; and
- wherein the material reservoir is a gravity fed inhalation fluid material storage tube extending above the electrically conductive foil.

* * * * *